US00PP16631P2

(12) United States Plant Patent
Olesen

(10) Patent No.: US PP16,631 P2
(45) Date of Patent: Jun. 13, 2006

(54) COMPACT FLORIBUNDA ROSE PLANT NAMED 'POULPAL019'

(50) Latin Name: ***Rosa* hybrid**
Varietal Denomination: Poulpal019

(75) Inventor: Mogens Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 101 days.

(21) Appl. No.: 11/001,915

(22) Filed: Dec. 1, 2004

(51) Int. Cl.
*A01H 5/00* (2006.01)

(52) U.S. Cl. ..... Plt./148
(58) Field of Classification Search ..... Plt./148, Plt./149, 107
See application file for complete search history.

*Primary Examiner*—Anne Marie Grunberg
*Assistant Examiner*—June Hwu

(57) ABSTRACT

A new garden rose plant of the floribunda class which has abundant, pink flowers and attractive foliage. This new and distinct variety has shown to be uniform and stable in the resulting generations from asexual propagation.

1 Drawing Sheet

SUMMARY OF THE INVENTION

Botanical classification: *Rosa* hybrid.

Variety denomination: 'Paulpal019'.

The present invention constitutes a new and distinct variety of garden rose plant that originated from a controlled crossing between the female seed parent 'Poulmanti', described and illustrated in U.S. Plant Pat. No. 11,540 issued Oct. 3, 2000, and the male pollen parent, an unnamed seedling from the same inventor.

The two parents were crossed during the summer of 1997, and the resulting seeds were planted in a controlled environment in Fredensborg, Denmark. The new variety is named 'Poulpal019'.

The new variety may be distinguished from its female seed parent, 'Poulmanti' by the following combination of characteristics:

1. While the seed parent 'Poulmanti' has petal count of 40 to 50, 'Poulpal019' has 55 to 60 petals.
2. The upper surface of the outer flower petals on 'Poulmanti' are Red Group 55B–55C. 'Poulpal019' is White Group 155B with a faint overlay of Red-Purple Group 62D.

The new variety may be distinguished from its male pollen parent by the following combination of characteristics:

1. The pollen parent has a red flower color, while flowers of 'Poulpal019' are medium pink.
2. The pollen parent has a flower diameter of 40 mm. Flowers of 'Poulpal019' are 60 to 65 mm.

The objective of the hybridization of this rose variety was to create a new and distinct variety for garden use with unique qualities, such as:

1. Uniform and abundant pink flowers;
2. Vigorous, but compact growth;
3. Disease resistance;
4. Large flower size;
5. Dark glossy foliage.

This combination of qualities is not present in previously available commercial cultivars of this type, known to the inventors, and distinguish 'Poulpal019' from all other varieties of which we are aware.

As part of the rose development program, Mogens N. Olesen germinated the seeds from the aforementioned hybridization during winter of 1997 and conducted evaluations on the resulting seedlings in a controlled environment in Fredensborg, Denmark.

'Poulpal019' was selected in the spring of 1998 by the inventor as a single plant from the progeny of the aforementioned hybridization.

Asexual reproduction of 'Poulpal019' by traditional budding and rooted cuttings was first done by Mogens N. Olesen in the nursery in Fredensborg, Denmark in July 1998. This initial and other subsequent asexual propagations conducted in controlled environments have demonstrated that the characteristics of 'Poulpal019' are true to type and are tranmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'Poulpal019'. Specifically illustrated in the drawing:

FIG. 1.1; Stem showing attachment of leaves, open flower and flower buds upon opening.

FIG. 1.2; Sepals, receptacle, and peduncle;

FIG. 1.3; Open flower from above, and flower petals, detached;

FIG. 1.4; Juvenile growth, showing anthocyanin on leaves;

FIG. 1.5; Upper surface of mature leaf;

FIG. 1.6; Bare stems exhibiting thorns.

DETAILED DESCRIPTION OF THE VARIETY

The following is a description of 'Poulpal019', as observed in its growth in a field nursery in Jackson County, Oreg. Observed plants are 3 years of age, and were grown on *Rosa multiflora* understock. Color references are made using The Royal Horticultural Society (London, England)

Colour Chart, 1995, except where common terms of color are used.

For a comparison, several physical characteristics of the rose variety 'Poulac007', a rose variety from the same inventors described and illustrated in U.S. Plant Pat. No. 15,794, are compared to 'Poulpal019' in Chart 1.

CHART 1

| | 'Poulpal019' | 'Poulac007' |
|---|---|---|
| General tonality of flower | Red Group 55A | Red Group 50D |
| Flower diameter size | 60 to 65 mm | 70 to 75 |
| Petal Size | 30 mm (l) × 26 mm (w). | 36 to 40 mm in length by 31 to 39 mm wide. |

FLOWER AND FLOWER BUD

Blooming habit: Continuous.

Flower bud:

*Size.*—Upon opening, 19 mm in length from base of receptacle to end of bud. Bud diameter is 13 mm.

*Bud form.*—Globular.

*Bud color.*—As sepals unfold, petals have distinct intronations of Yellow-Green Group 145D, Red-Purple Group 65D, and Orange-White Group 159C.

*Sepal inner surface.*—Color: Yellow-Green Group 145C and 145B with intonations of Greyed-Red Group 182A. Surface: Medium pubesecence observed.

*Sepal outer surface.*—Color: Yellow-Green Group 144A. Anthocyanic pigments the color of Greyed-Red Group 182A observed. Texture: Rough with many stipitate glands.

*Sepal shape.*—Apex: Cirrhose. Base: Flat at union with receptacle.

*Sepal margin.*—Medium foliaceous appendages on three of the five sepals.

*Sepal size.*—23 mm (l)×8mm (w).

*Receptacle.*—Texture: Smooth and Glabrous. Shape: Funnel shaped. Size: 5 mm (h)×8 mm (w). Color: Yellow-Green Group 144A.

*Peduncle.*—Length: 60 to 90 mm in length from the base of the peduncle to flowering portion. Texture: Smooth. Color: Yellow-Green Group 146A.

*Pedicel.*—Surface: Rough with stipitate glands. Length: 35 to 40 mm. Diameter: 3 mm on average. Color: Yellow-Green Group 145B and Yellow-Green Group 144A. Anthocycanic pigments Greyed-Red 181B. Strength: Strong.

Flower bud development: Flower buds are borne in clusters of 3 to 5 flower buds per stem. Inflorescence type is a corymb.

Flower bloom:

*Fragrance.*—

*Duration.*—The blooms have a duration on the plant of approximately 7 to 10 days. After flowers have matured completely, petals fall away from plant.

*Size.*—Flower diameter is 60 to 65 mm when open. Flower depth is 30 mm.

*Flower shape.*—Upon opening flower petals retain globular shape with a tight center. As flowers mature, petals curve out from the center, forming a rosette to an open cup.

*Shape of flower, side view.*—Upon opening, Upper portion: Flat. Lower portion: Concave. After opening, Upper portion: Flattened convex. Lower portion: Concave.

Petalage: Under normal conditions, flowers have 55 to 60 petals total, 10 to 15 of which are petaloids.

Petal color:

*Upon opening, outer petals.*—Upper surface: At marginal zone, Yellow-White Group 158C blended with Red-Purple Group 62D. At the basal zone, Yellow-White Group 158C. Lower surface: Red-Purple Group 68A with random speckles of Yellow-White Group 158C.

*Upon opening, inner petals.*—Upper surface: At the marginal zone, Red-Purple Group 62C, blending with Yellow-White Group 158B at the middle and marginal zone. Lower surface: Red Group 55A blended with Red-Purple Group 58D. Occasionally there are streaks the color of Orange-White Group 159A bisecting the petal and occurring at random throughout the petal.

*Basal petal spots, upon opening.*—Upper surface: Yellow Group 4B to Yellow Group 4A. Lower surface: Yellow Group 4B to Yellow Group 4A.

*After opening, outer petals.*—Upper surface: White Group 155B with a faint overlay of Red-Purple Group 62D. Lower surface: Red-Purple Group 68D with random streaks of Orange-White Group 159D.

*After opening, inner petals.*—Upper surfaces: White Group 155B with a faint overlay of Red-Purple group 65C. Lower surface: Red-Purple group 68C with streaks of Yellow-White Group 158D bisecting the petal at random throughout.

*Basal petal spots, after opening.*—Upper surface: Yellow Group 4B. Lower surface: Yellow Group 4B.

General tonality: On open flower at the flower center Red Group 55A, toward the edges Red-Purple Group 65C to White Group 155A. No change in the general tonality at the end of the $10^{th}$ day. Afterwards, general tonality is White Group 155A.

Petals:

*Petal reflex.*—Somewhat reflexed.

*Margin.*—Entire and uniform.

*Shape.*—Generally narrow elliptical to orbicular in shape. Apex: Orbicular. Base: Obtuse.

*Size.*—30 mm (l)×26 mm (w).

*Texture.*—Smooth.

*Thickness.*—Average.

Petaloids:

*Quantity.*—Normally 10 to 15.

*Shape.*—Irregular and elliptical.

*Color.*—Upper surface: Orange Group 27A with overlay of Red Group 38A at margins. Basal petal spots are Yellow Group 4A. Lower surface: Red Group 52B. Basal petal spots are Yellow Group 4A.

*Size.*—13 mm (l)×4 mm (w).

Reproductive organs:

*Pollen.*—None observed.

*Anthers.*—Size: 2 mm in length. Color: Yellow group 11B at the center, margins are Yellow-Orange Group 21A. Quantity: 150 (actual count).

*Filaments.*—Color: Yellow Group 12B. Length: 10 to 12 mm.

*Pistils.*—Length: 7 to 9 mm. Quantity: 80 (actual count).

*Stigmas.*—Slightly superior in location relative to the length of the filaments and the height of the anthers. Color: Greyed-Yellow 162D.

*Styles.*—Color: Red-Purple Group 64A.
*Hips.*—None observed.

PLANT

Plant growth: Moderate, upright to bushy. When grown as a budded field grown plant on *Rosa multiflora* understock, the average height of the plant is 40 to 60 cm. Average spread is 40 cm.

Stems:
*Color.*—Juvenile growth: Yellow-Green Group 146B. Mature growth: Yellow-Green Group 146A.
*Length.*—On average, canes are 35 cm from the base of the plant to the flowering portion.
*Diameter.*—6 mm.
*Internodes.*—On mature canes, there is an average distance of 30 mm between nodes.
*Surface texture.*—Young wood: Smooth. Older wood: Smooth.

Thorns:
*Incidence.*—11 thorns per 10 cm of stem.
*Size.*—Normally 9 mm.
*Shape.*—Upper size: Concave to flat. Lower side: Concave.
*Color.*—Juvenile thorns: Yellow-Green Group 151A to Yellow-Green Group 144C. Mature thorns: Greyed-Yellow Group with intonations of Greyed-Red 161A Group 179B.

Plant foliage: Normally 7 leaflets on compound leaves.
*Compound leaf.*—100 mm (l)×60 (w).
*Quantity.*—3 leaves per 10 cm of stem on average.
*Color of mature foliage.*—Upper side: Green Group 137A to Yellow-Green Group 147A. Lower side: Yellow-Green Group 147B.
*Color of juvenile foliage.*—Upper side: Yellow-Green Group 146B with anthocyanic intonations at the leaflet margins, the color of Greyed-Red Group 178A. Lower side: Yellow Green Group 146B.

Plant leaves and leaflets:
*Stipules.*—Size: 17 mm in length. Shape: Linear, slightly broad based with outward extending apecies. Margins: Finely serrated with few stipitate glands. Color: Green Group 137A.
*Petiole.*—Length: 15 mm. Diameter: 2 mm.
*Upper surface.*—Color: Yellow-Green Group 145B.
*Lower surface.*—Color: Yellow-Green Group 145A. Observations: Smooth.
*Rachis.*—Length: 50 mm. Upper surface: Color: Yellow-Green Group 144A.
*Lower surface.*—Color: Yellow-Green Group 145A. Observations: Small prickles observed.
*Leaflet.*—Edge: Finely serrated. Size: Average size of the terminal leaflet on normal leaves is 35 mm (l)×23 mm (w). Shape: Elliptic. Base: Obtuse. Apex: Acuminate. Texture: Smooth. Thickness: Average. Arrangement: Odd pinnate. Venation: Reticulate. Glossiness: Somewhat glossy.

Disease resistance: Above average resistance to powdery and downy mildew, rust, black spot, and Botrytis under normal conditions in Jackson County, Oreg.

Cold hardiness: The variety 'Poulpal019' has been found to be cold tolerant to USDA Cold Hardiness Zone; 6.

It is claimed:

1. A new and distinct variety of rose plant of the floribunda rose class named 'Poulpal019', illustrated and described herein as a distinct and novel rose variety due to its abundant pink flowers, dark green foliage, disease resistance and extended period of bloom.

* * * * *

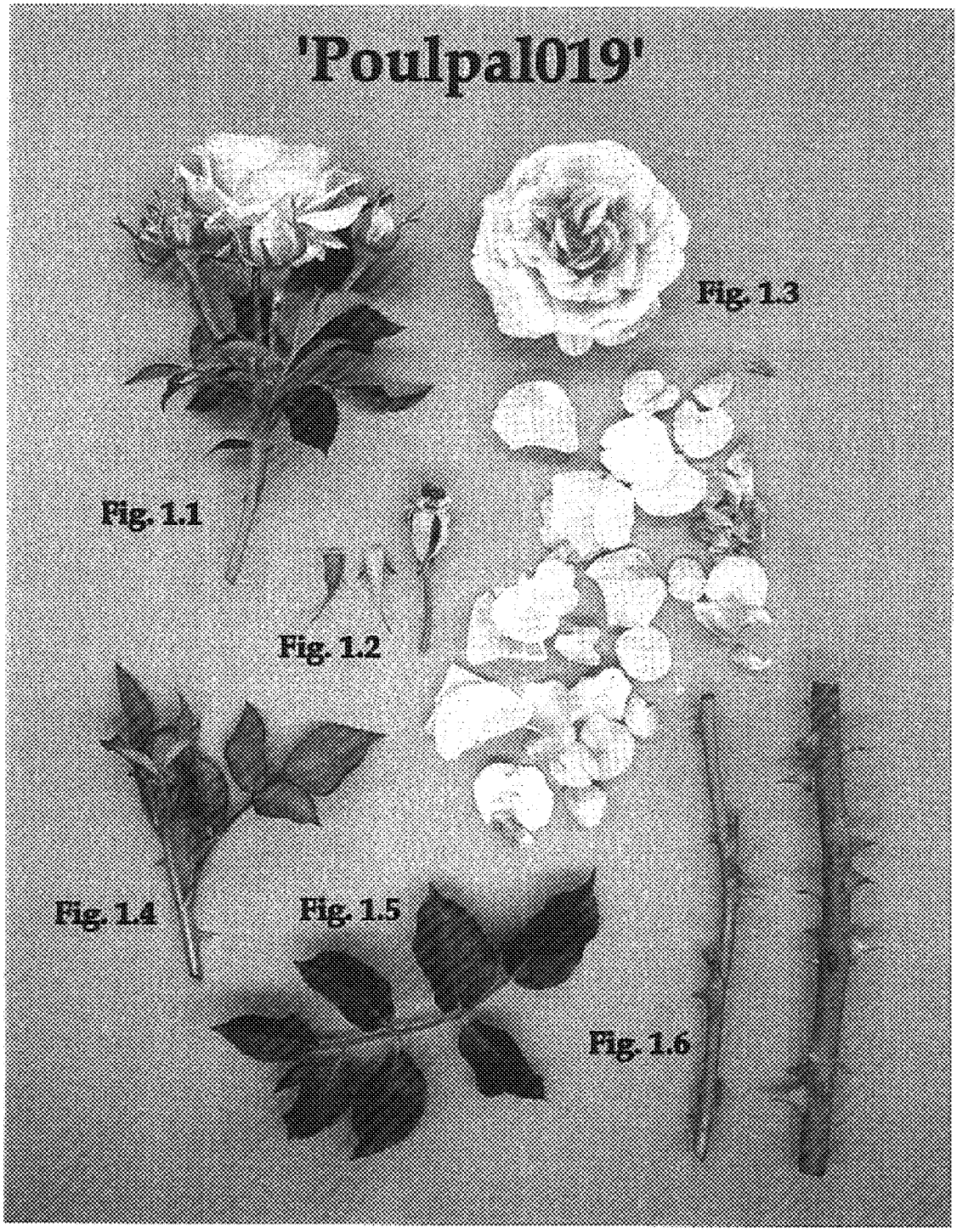
'Poulpal019'
Fig. 1.1
Fig. 1.2
Fig. 1.3
Fig. 1.4
Fig. 1.5
Fig. 1.6